(12) United States Patent
Garito et al.

(10) Patent No.: US 7,507,232 B1
(45) Date of Patent: Mar. 24, 2009

(54) FLEXIBLE ELECTROSURGICAL ELECTRODE WITH MANIPULATOR

(75) Inventors: Jon C. Garito, Oceanside, NY (US); Alan G. Ellman, Oceanside, NY (US)

(73) Assignee: Elliquence, LLC, Oceanside, NY (US)

( * ) Notice: Subject to any disclaimer, the term of this patent is extended or adjusted under 35 U.S.C. 154(b) by 305 days.

(21) Appl. No.: 11/357,251

(22) Filed: Feb. 21, 2006

Related U.S. Application Data

(63) Continuation-in-part of application No. 10/914,740, filed on Aug. 9, 2004, now Pat. No. 7,160,295.

(51) Int. Cl.
*A61B 18/18* (2006.01)
*A61B 18/14* (2006.01)

(52) U.S. Cl. .............................. 606/15; 606/41; 606/45; 606/46; 606/49

(58) Field of Classification Search .................... 606/45, 606/46, 49, 15, 41
See application file for complete search history.

(56) References Cited

U.S. PATENT DOCUMENTS

| | | | | |
|---|---|---|---|---|
| 5,217,460 A | * | 6/1993 | Knoepfler | 606/52 |
| 5,360,428 A | * | 11/1994 | Hutchinson, Jr. | 606/45 |
| 5,364,393 A | * | 11/1994 | Auth et al. | 606/34 |
| 5,441,499 A | * | 8/1995 | Fritzsch | 606/45 |
| 6,280,441 B1 | * | 8/2001 | Ryan | 606/45 |

\* cited by examiner

*Primary Examiner*—Lee S Cohen

(57) ABSTRACT

An electrosurgical instrument that is configured for use in MIS electrosurgical procedures, comprises a handpiece with a separable electrosurgical electrode in the form of a micro-fiber, comprising a long, thin, flexible, insulated wire. The combination is configured to cooperate with the cannula of an endoscope to reach interior tissue. The handpiece is constructed to allow the tip with the micro-fiber active end to be deflected to navigate the fiber end in diverse directions under control of the user, and also allows the deflected position to be releasably clamped with the same hand that manipulates the micro-fiber active end.

17 Claims, 3 Drawing Sheets

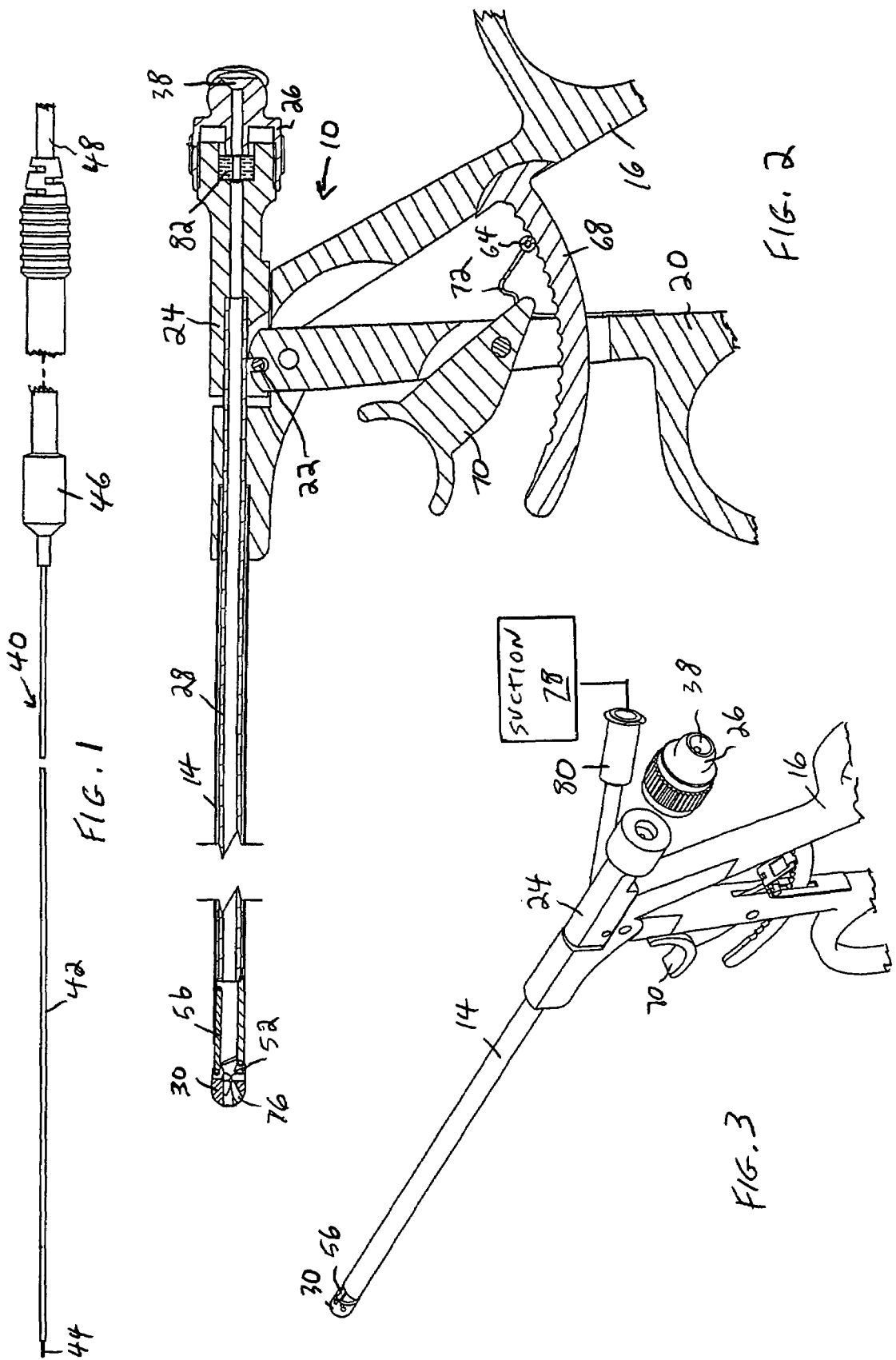

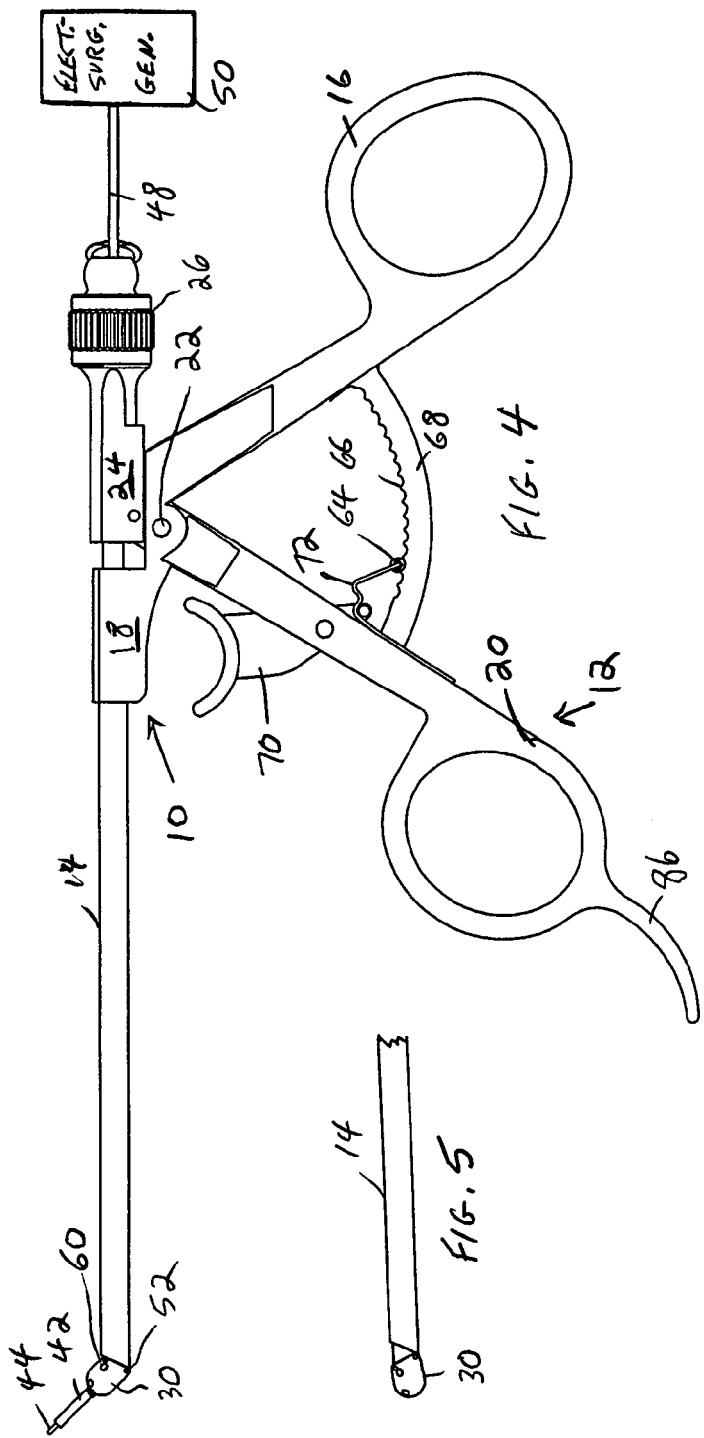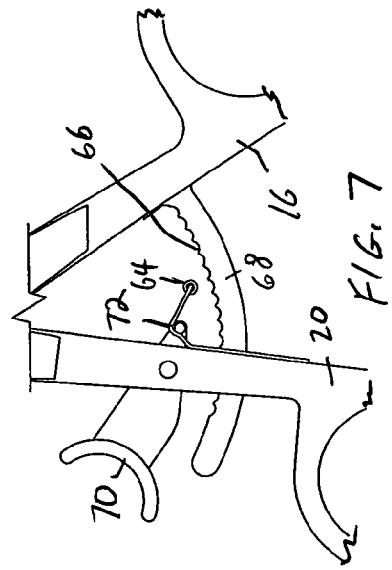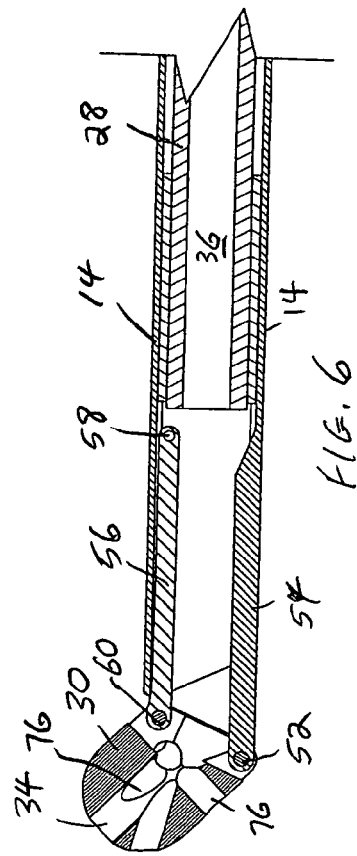

FLEXIBLE ELECTROSURGICAL ELECTRODE WITH MANIPULATOR

RELATED APPLICATION

This application is a CONTINUATION-IN-PART of a commonly owned patent application, Ser. No. 10/914,740, filed in the U.S. Patent And Trademark Office on Aug. 9, 2004 and entitled FLEXIBLE ELECTROSURGICAL ELECTRODE FOR TREATING TISSUE, now U.S. Pat. No. 7,160,295.

This invention relates to an electrosurgical probe for treating ailments or diseases by minimally invasive surgery (MIS) or similar endoscopy procedures.

BACKGROUND OF THE INVENTION

Our prior U.S. Pat. No. 5,505,728, whose contents are incorporated herein by reference, describes a novel electrosurgical electrode for ablating or shrinking throat tissue in a surgical procedure. This is accomplished by an electrosurgical electrode activated by electrosurgical currents that is applied by the surgeon to the patient.

Our prior U.S. Pat. No. 6,447,510, whose contents are incorporated herein by reference, describes a novel electrosurgical electrode for the treatment of benign and malignant lesions of the upper aerodigestive tract. This is accomplished by an electrosurgical electrode activated by electrosurgical currents and configured such that it can be applied by the surgeon to the patient via the rigid cannula of a laryngopharyngoscope. The electrode is stiff and specifically configured for this particular procedure.

Our prior U.S. Pat. No. 6,231,571, whose contents are incorporated herein by reference, describes a novel electrosurgical handpiece employing an extendible/retractable electrode operable by the surgeon for manipulating the working end of the electrode to reach treatment sites that may not be more directly accessible. The examples given include spinal surgery.

Our parent application, the contents of which are herein incorporated by reference, describes the use of a micro-fibre electrode, a very thin, flexible electrically-insulated wire, typically about 1 mm or less in diameter and a length of about 475 mm or more, that will fit down a working channel of an endoscope and thus access patient sites not easily reachable with ordinary electrosurgical electrodes, such as the larynx, or for snaking through a vein. The micro-fibre probes when used with RF electrosurgery are highly suitable for the selective, superficial removal of mucosal lesions and providing a sound specimen for histological examination and providing the least amount of collateral injury. This is very advantageous along with significantly reducing the costs for these procedures and greatly reducing scars and synechiae.

There is still a need in the art for devices to simplify the treatment by MIS of tissues more easily reachable than with the electrodes described in the referenced patents. These include, among others, epidural scar tissue, adhesions and other pathology, spinal diseases such as intradiscal shrinkage or ablation, endoscopic endonasal procedures, as well as treating internal tissues reachable only by, for example, being snaked or threaded up into a vein to travel up to leg lesions, etc.

Specially designed small knives and micro-scissors are available for traditional tissue ablation in the larynx and trachea. However, their disadvantage is that they require expert manual skills and rigorous practice, and in addition frequently result in diffuse bleeding at the surgical site, obscuring the operative field and making it difficult to access the progress of the surgery. Powered instruments (micro-debriders, shavers) have been used, in which tissue is excised by a rotating blade and aspirated out of the sheath, but there is a high risk of tissue damage and tissue may be chewed up rapidly and cannot be evaluated histologically. Lasers such as the $CO_2$ have become popular for use in endoscopic surgery of the larynx and trachea. Their disadvantages include combustion of ventilation tube materials and anesthetic gas mixtures during laser use in larynx tissue destruction and alteration, complicated safety precautions for doctors, staff and patients (ie. protective glasses, bouncing of the laser beam off metal instruments causing inadvertent burns) and possible electrical hazards, eye and skin injuries, as well a steep learning curve for doctor and staff, and their high price.

SUMMARY OF THE INVENTION

An object of the invention is an improved electrosurgical probe for treating tissue based on the use of the micro-fibre electrode.

Another object of the invention is an improved probe for treating tissue that can use a standard operating room working channel fiberoptic scope or endoscope.

Still another object of the invention is an improved electrosurgical probe that can be used with a microlayrngoscope.

In accordance with a feature of the invention, an electrosurgical probe comprises a very long, thin, flexible, insulated wire electrode, so thin and flexible that it can be used with a miniature or micro-sized endoscope combining imaging optics and an instrument channel with an overall diameter below about 3 mm, hereinafter referred to as a micro-fibre. In accordance with a principal feature of the present invention, the micro-fibre electrode is removably mounted in a novel handpiece or handle for controlling the micro-fibre electrode while also being able to manipulate and guide the micro-fibre electrode in a relatively stationary, tissue touching technique, improving surgical outcomes in procedures such as endolaryngeal surgery. The combination of the micro-fibre electrode with the novel handpiece results in an innovative endoscopic instrument allowing precise, accurate cutting and coagulation of laryngeal lesions, for example, when hand manipulating the micro-fibre tip and thus being able to navigate and guide the micro-fibre tip more easily to the targeted tissue. The targeted tissue can be removed, ablated, vaporized, coagulated, incised, or excised where histological examination is required. The movement range of the preferred instrument allows the micro-fibre electrode tip to be moved from a neutral position aligned with the longitudinal axis of the handpiece in an upward direction about 45° or down about 15°, allowing access to a wide range of targeted lesions in a wide range of locations on a patient's anatomy.

The micro-fibre electrode handpiece that serves as the manipulator device offers many significant clinical and technical advantages with video endoscopic assisted instrumentations. The advantages include safety, tactile feedback, wide range of accessibility, bloodless field, precise and accurate removal of targeted tissue, much less scarring, faster, high quality healing, excellent tactile feedback, and less pain and swelling. Pressureless cuts minimize the risk of injury to laryngeal structures. Economically it combines a shorter operating time with a cost effective unit and instrument. A further advantage is the ability to excise tissue for histologic evaluation if desired.

A further important feature of the combined manipulator and separable micro-fiber electrode is that the micro-fiber electrode can be made inexpensively and thus as a simple disposable single use surgical product. It is important for several reasons, such as safety and preventing transfer of germs, to use disposable surgical instruments wherever feasible. Known endoscopic instruments, due to their complexity, size and high material costs, are expensive to design and make, thus rendering disposable single patient use unlikely. A second problem is autoclavability. Cleaning the known complex tubing and mechanisms is difficult. Sterilizing them often causes breakdown and surgical failures.

The micro-fiber electrode used in the invention is simple to construct, and uses a minimal amount of precious material. It therefore provides a safe, sterile, surgical, disposable single patient use tool available for each patient in a cost effective manner. The manipulator of the invention in which it is used, while relatively less expensive to construct than re-useable surgical tools, has the big advantage that the re-usable manipulator is only the navigating guide and holder for the disposable RF micro-fiber electrode which actually contacts the tissue surgically. Thus sterilization of the manipulator is much less of a problem for the surgeon and hospital and contributes to patient safety.

In a preferred embodiment, the handpiece is constructed such that, not only can the working end be deflected after insertion in the patient, but also the deflected position can be clamped by the surgeon, with its position easily changed by the surgeon with a finger of the same hand upon releasing the clamp whenever desired. The length that the fibre extends from the end of the deflector can also be easily controlled in the handpiece of the invention.

In another preferred embodiment, the elongated probe comprises at its distal end an exposed blunt wire end.

In still another preferred embodiment, the elongated probe comprises at its distal end an exposed shaped member connected to a wire end. Preferably, the shaped member can have in front an American football shape or a bullet shape, which is especially useful for endonasal procedures.

In still another preferred embodiment, the manipulator is configured to provide a channel for suctioning off separated tissue or plume or other fluids created at the surgical site. The reduced plume/fluids at the site improves visibility for the surgeon.

Preferably, the overall outside diameter of the electrosurgical electrode of the invention is 1 mm or less, and it has an overall length, measured from the connector, of at least about 475 mm, preferably, about 600 mm for certain procedures, especially spinal procedures, but for treating endonasal tissues that can be reached with a shorter electrode a length of at least about 150 mm is preferred. A longer length of at least about 280 mm is generally preferred for most procedures. For such procedures, a maximum diameter of about 0.06 mm can be used.

By "proximal" is meant the end closest to the connector, and by "distal" is meant the end furthest from the connector.

The construction of the invention will provide important benefits for all MIS arthroscopic or endoscopic procedures and in many cases enables the efficient delivery of radiofrequency (RF) energy technology for controlled precise tissue cutting, absorption and other tissue effects and in a safe manner. It is cost effective and considerably less expensive than other surgical modalities such as lasers where the novel electrode configuration may be of importance, as well as for general electrosurgical procedures where the volumetric reduction of tissue or ablation of tissue that is hard to reach with the known electrodes is desirable. Examples of particular procedures for which the electrosurgical electrode of the invention is particularly suitable is spinal disc reduction and endonasal procedures.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals designating the same or similar elements.

BRIEF DESCRIPTION OF THE DRAWINGS

In the drawings:

FIG. 1 is a side view of one form of an electrosurgical micro-fibre electrode for use in the manipulator according to the invention;

FIG. 2 is a side and partially cross-sectional view of one form of an electrosurgical manipulator in accordance with the invention;

FIG. 3 is a partial perspective exploded view of the handle end of the manipulator of FIG. 2;

FIG. 4 is a side view of the working end of the manipulator of FIG. 2 with the micro-fibre inserted and with the working end deflected upward;

FIG. 5 is side view of just the working end shown deflected downward;

FIG. 6 is an enlarged cross-sectional view of the working end of the manipulator shown in the same upward-deflected view as in FIG. 4 but without the fibre electrode;

FIG. 7 is a partial side view showing the handle release lever in the disengaged position;

DETAILED DESCRIPTION OF PREFERRED EMBODIMENTS

Figure 8:
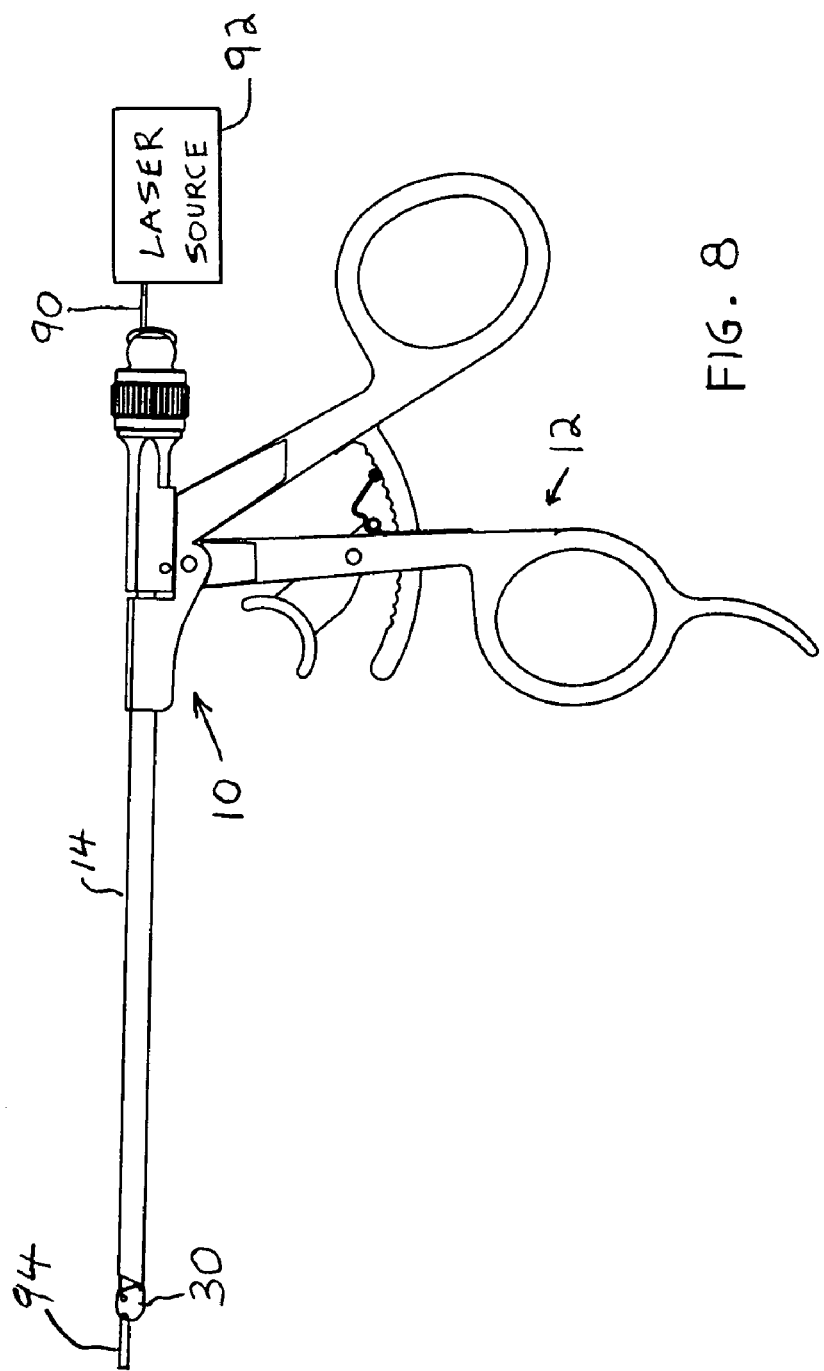
FIG. 8 is a view similar to FIG. 4 except that a laser fibre has been substituted for an electrosurgical fibre.

The reader is directed to the referenced prior patents for a more detailed description of electrosurgical procedures and principles of operation which will assist in understanding the invention described in the present application.

As described in the co-pending application, a very thin electrosurgical electrode in the form of a fibre, referred to herein as a micro-fibre, is provided for use with a miniature micro endoscope. The present invention describes a novel manipulator which receives the micro-fibre and in turn is sufficiently thin to fit in a channel of a miniature micro endoscope in order to allow the operating surgeon to control the position of the active end of the fibre while inside the patient or at the surgical site.

In a preferred embodiment illustrated in the figures, the manipulator 10 in accordance with the invention comprises a proximal handle end 12 to which is mounted an elongated tubular-shaped outer tube 14. The right handle half 16 is connected to a body part 18 on which the left handle part 20 is pivotably mounted, shown at 22. The outer tube 14 is fixedly mounted to the body part 18, on which is slidably mounted a rear section 24 to which is connected the left handle part 20. As the left handle part 20 is pivoted with respect to the right handle part 16, the rear section 24 slides axially, horizontally in FIG. 4, i.e., in the same direction as the longitudinal axis of the manipulator, which is likewise horizontal. The rear or proximal end of the manipulator 10 is closed of by a channel port fitting 26 which is threadingly mounted on the end of the rear section 24.

Inside of the outer tube 14 is mounted an inner tube 28 shown more clearly in FIGS. 2 and 6. The proximal end of the inner tube is anchored to the movable handle 20 and to the rear section 24 such that, as the movable handle pivots with respect to the fixed handle 16, the inner tube 28 slides a short distance axially within the outer tube 14 as the rear section translates horizontally. At the distal end of the outer tube is mounted a deflector tip 30. An axially-aligned common bore is formed by an aperture 34 in the deflector tip 30 connected to a bore 36 in the inner tube 28 and an aperture 38 in the channel port fitting 26. Through this common bore via the end aperture 38 can be threaded a removable micro-fibre 40 of the type illustrated in FIG. 1, which comprises a long thin electrically-insulated wire 42 except for a small section 44 at the distal end of the wire which is left bare and electrically exposed. That bare end 44 is the working or active end of this form of the electrode. The right end or proximal end is fitted with a connector 46 to which a cable 48 can be connected, the latter in turn can be connected to conventional electrosurgical apparatus 50, illustrated schematically in FIG. 4. In a typical geometry, the overall length of the manipulator of FIG. 2 is about 10-12 inches, and the fibre 40 can be about 2 feet long so that it can be separately usable alone or with other instruments. As shown in FIG. 4, in operation, the active fibre electrosurgical end 44 protrudes from the bore 34 in the deflector tip 30. The desired operation is to deflect the tip 30 upward and downward under control of the surgeon so as to direct the active fibre end 44 to different surgical sites as needed by the surgeon. This is useful especially in those situations where the surgical site cannot be directly accessed when the deflector tip 30 holding the fibre electrode is axially aligned in its rest position shown in FIG. 2.

A preferred form of the deflection mechanism is illustrated in the drawings and is accomplished as follows. The deflector tip 30 pivots about a pin 52 anchored to a lug 54 welded to the distal end of the outer tube (FIG. 6), and thus that edge of the tip 30 only rotates about the pivot pin 52 axis. The pivot point 52 is visible in the assembly drawing of FIG. 4. An actuator slide bar or link 56 is anchored by a pivot pin 58 to the distal end of the inner tube 28. The distal end of the actuator link is in turn pivoted by way of a pivot pin 60 to an upper part of the deflector tip 30, so as the slide bar 56 slides forwards and backwards, it pushes or pulls the actuator link in the same respective direction. The net result is that the tip 30 carrying the flexible fibre electrode 42 deflects down or up in discrete steps (the number depending on the pitch of the curved rack teeth—described below) depending upon whether the slide bar 56 and inner tube 28 is pushed or pulled as the handle parts 20, 16 are moved together or apart, respectively. FIG. 2 shows the handle parts in their neutral position with the deflector tip axially aligned. FIG. 5 shows the deflector tip downwardly deflected, and FIGS. 4 and 6 show the deflector tip upwardly deflected.

During all of such movements, handle parts 20, 16 are maintained in their selected position by means of a ratchet roller 64 that engages a slot between teeth 66 in a rack 68 fixed to the rear handle part 16, with the result that the position last occupied is held in place or locked temporarily by this action. The ratchet roller 64 moves in either direction along the rack slots. When, however, the surgeon presses a lever release 70 the lever end lifts the roller 64 (FIG. 7) out of a rack slot and the handles move into their neutral or rest position by the action of spring 72 built into the ratchet mechanism. In the neutral position, the fibre is longitudinally aligned with the longitudinal axis of the tubular structure and thus points directly forward. The two pivot pins 52, 60 on the deflector tip 30 are visible in the assembly view of FIG. 4, but the third pivot 58 on the slide bar 56 is not, as it is hidden inside of the outer tube. The spring 72 pressure is chosen so that any handle position is locked in place so that the surgeon can address the targeted tissue with the activated fibre end, but it requires only a relatively small hand grip pressure to change the handle positions and thus the deflected position of the deflector tip. Similarly, a relatively small finger pressure on lever 70 is needed to release the handles so that the fibre can be returned to its neutral position, needed, for example, when it becomes desirable to remove the tube 14 from the endoscope channel (not shown).

The intended use of the manipulator handpiece of the invention is to allow a surgeon in an endoscopic procedure to remotely manipulate the tip of a small diameter flexible fiber electrode inside the human body using one hand to hold and cause deflection of the fiber tip and to be able to use one finger from the same hand to engage or disengage a ratchet lock on the deflector tip position.

The rear half of the handle is fixed, and the forward half of the handle is movable from the two positions illustrated in FIGS. 2 and 4. The small finger lever 86 at the bottom of the movable handle part together with the finger hole above it allows the movable handle part to be moved relative to the fixed handle part both toward and away from the latter. When the two handle parts are spread apart (FIG. 4), the inner tube 28 is retracted into the outer tube 14 which pulls the deflector actuation link 56 backwards and pivots the deflector tip 30 upwards. When the two handle parts are brought together (FIG. 2), the inner tube is extended from the outer tube which pushes the deflector actuation link forwards and pivots the deflector tip downwards. The flexible fibre whose bare end extends out from the central bore of the deflector tip follows the tip deflections and thus faces in directions extending over a range of about 15° (downwards) to about 45° (upwards) totaling about 60°.

Ventilation holes 76 in the deflector tip 30 allow for suction of smoke and gases, via a conventional suction apparatus 78 connected via a luer suction port 80 to the inner channel 36, that may be generated by the activated electrosurgical fiber at the surgical site.

As will be noted, the separable flexible fiber, which can for example be about 1 millimeter in diameter passes through the device from the channel cap 26 end. Loading of the fiber is done with the deflector tip in the straight ahead position and the cap in a loosened position. After the fiber has been loaded, the cap is tightened. A fiber channel seal, shown at 82, of resilient material, when the cap is tightened, not only clamps the fibre end to the slidable part 24 so that the former moves in unison with the latter, but also functions to seal off the end cap 26 from any smoke or fumes suctioned up the tube by the suction apparatus 78.

The exposed fibre bare end 44 is preferably equal to or less than about 1 mm, and can be as small as 0.125 mm. The insulating coating adds only about 0.15 mm. For certain procedures, the end should be blunt so it will more easily pass through the fiber channel. The fiber is sufficiently thin and flexible, but sufficiently stiff, that it can be used with an ordinary or a miniature micro endoscope and in addition can even be snaked down or threaded up into a vein to reach, e.g., leg lesions. It has sufficient resilience that, if bent, it will spring back to its initial position. For these applications, the overall diameter of the sheathed wire should be about 1 mm or less, and it should have an overall length, measured from the connector 46, of at least about 475 mm, preferably, about 600 mm. The outer tube can have a small enough diameter that it can be used with a miniature micro endoscope whose channel is typically less than about 3 mm.

The invention is important for spinal surgery, for example, targeted treatment of epidural scar tissue, adhesions and other pathology, or for precise intradiscal shrinkage or ablation.

A further advantage is obtained when the electrode of the invention is used with electrosurgical apparatus capable of generating RF electrosurgical currents at frequencies of about 4 MHz. The monopolar electrode wire thus enables the efficient delivery of RF energy and is uniquely suited for spinal procedures, such as myeioscopy or endoscopic epiduraplasty, due to the controlled precise tissue absorption and versatile tissue effects and safety it affords. The resultant technology is cost effective and offers the further advantage that it delivers lower tissue temperature profiles. Moreover, it allows more easily the extension of RF electrosurgical currents to minimal and micro invasive surgical procedures. Minimal and micro surgical procedures typically result in reduced pain and scarring, shorter recovery time and increased effectiveness compared to traditional surgical procedures. Most of the pain associated with traditional surgery procedures results from the cutting of layers of skin and muscle tissue, which also delays healing and generates high levels of pain. An example of suitable electrosurgical apparatus is the Model SURGITRON Dual-Frequency electrosurgical unit manufactured by and available from Ellman International, Inc. of Oceanside, N.Y.

It will also be appreciated that the manipulator 10 of the invention also can be combined with a laser fibre in place of an electrosurgical fibre and used in exactly the same way as the electrosurgical fibre. This is illustrated in FIG. 8, showing a laser fibre 90 extending from and optically coupled to a laser source 92, threaded through the hollow tube 14 such that the fibre's free end 94 extends through the deflector tip 30 and can be oriented in the same manner as the electrosurgical fibre of FIG. 4.

While the blunt wire end is the most versatile, it may be desirable to provide a small ball at the distal end for easier threading through a vein.

A further important application for the electrosurgical electrode of the invention is in the treatment more specifically for endoscopic endonasal surgery with RF electrosurgical currents, preferably at about 34 MHz. The electrosurgical electrode of the invention can easily accomplish the same ablative, vaporizing, and debulking of diseased tissue within the nasal cavity, but with the benefits described above. For such applications, we prefer an electrically-insulated fibre that comprises a generally American football-shaped or bullet-shaped electrically-conductive member affixed to the end of the wire to form the active end, as is described in the co pending application.

In this description, by "elongated" or "longitudinal" is meant parallel to the long axis of the electrode (horizontal in FIG. 2).

Once the surgeon has positioned the working end 44 of the electrode with respect to the tissue to be operated on, he or she then activates the electrosurgical apparatus 50 causing a discharge of unipolar currents between a ground plate (not shown) and the bare electrode end 44 capable of causing excision or ablation or shrinkage of tissue or cauterization of a blood vessel in the usual way. As with the embodiments of the prior patents, the insulating coating on the electrode 40 will prevent accidental touching of any conductive members or patient tissue by the electrode sides, so that the unipolar discharge is localized to the region surrounding the working end 44.

It will also be understood by persons of ordinary skill in the art that other mechanisms associated with a tubular structure for deflecting the tip 30 can be substituted for the preferred mechanism described and illustrated, and while the invention has been described in connection with such preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical handpiece for manipulating an electrosurgical fiber electrode for treating tissue, comprising:
   (a) an elongated first tubular member having a major longitudinal axis and having a proximal first end and a distal second end and containing an inner channel for receiving a wire electrode comprising a long thin flexible electrically-insulated wire having an active distal end,
   (b) a deflector tip mounted for pivotal movements on the distal second end of the first tubular member, the deflector tip having at least one hole through which the distal end of the wire electrode can pass and be exposed when inserted through the channel,
   (c) a handle connected to the first tubular member, the handle having a movable part,
   (d) means connecting the movable part of the handle to the deflector tip such that movements of the movable part of the handle are transmitted to the deflector tip causing the distal end of the wire electrode when inserted through the channel to extend in different orientations with respect to the longitudinal axis of the first tubular member,
   (e) further comprising a suction port for receiving external suction coupled to the inner channel of the first tubular member, the deflector tip further comprising additional openings such that any suctionable material arising from the treated tissue can be suctioned away via the inner channel and suction port.

2. The electrosurgical handpiece as claimed in claim 1, wherein the means of claim element (d) comprises an inner slidable member, an actuator link, a proximal end of the inner slidable member being connected to the movable part of the handle, a distal end of the inner slidable member being connected to a proximal end of the actuator link, a distal end of the actuator link being pivotably connected to one side of the deflector tip, the other side of the deflector tip being pivotably connected to a distal end of the first tubular member.

3. The electrosurgical handpiece as claimed in claim 2, wherein the inner slidable member comprises a second inner tubular member connecting the actuator link to the movable part of the handle.

4. The electrosurgical handpiece as claimed in claim 2, wherein the deflector tip is mounted on the first tubular member so as to allow the deflector tip to be pivoted in the plane of the pivotable connections over a range of about 60° with respect to the longitudinal axis of the tubular member.

5. The electrosurgical handpiece as claimed in claim 1, wherein the first tubular member is sized to fit within an endoscope.

6. An electrosurgical handpiece for manipulating an electrosurgical fiber electrode for treating tissue, comprising:
   (a) an elongated first tubular member having a major longitudinal axis and having a proximal first end and a distal second end and containing an inner channel for receiving a wire electrode comprising a long thin flexible electrically-insulated wire having an active distal end,
   (b) a deflector tip mounted for pivotal movements on the distal second end of the first tubular member, the deflector tip having at least one hole through which the distal end of the wire electrode can pass and be exposed when inserted through the channel,
   (c) a handle connected to the first tubular member, the handle having a movable part,
   (d) means connecting the movable part of the handle to the deflector tip such that movements of the movable part of the handle are transmitted to the deflector tip causing the distal end of the wire electrode when inserted through the channel to extend in different orientations with respect to the longitudinal axis of the first tubular member,
   (e) further comprising a removable cap mounted on the proximal end of the first tubular member, the removable cap having an opening through which the wire electrode can be passed from the outside into the channel, and means for applying clamping pressure to the wire electrode when present such that the longitudinal position of the wire electrode in the channel is maintained.

7. The electrosurgical handpiece as claimed in claim 6, wherein the means for applying clamping pressure comprises a resilient sealing member surrounding the wire electrode when present and mounted between the cap and the proximal end of the first tubular member when the cap is tightened.

8. The electrosurgical handpiece as claimed in claim 7, wherein the resilient sealing member is configured such that, when the cap is tightened, the proximal end of the first tubular member is sealed against the egress of suctionable material.

9. An electrosurgical handpiece for manipulating an electrosurgical fiber electrode for treating tissue, comprising:
  (a) an elongated first tubular member having a major longitudinal axis and having a proximal first end and a distal second end and containing an inner channel for receiving a wire electrode comprising a long thin flexible electrically-insulated wire having an active distal end,
  (b) a deflector tip mounted for pivotal movements on the distal second end of the first tubular member, the deflector tip having at least one hole through which the distal end of the wire electrode can pass and be exposed when inserted through the channel,
  (c) a handle connected to the first tubular member, the handle having a movable part,
  (d) means connecting the movable part of the handle to the deflector tip such that movements of the movable part of the handle are transmitted to the deflector tip causing the distal end of the wire electrode when inserted through the channel to extend in different orientations with respect to the longitudinal axis of the first tubular member,
  (e) wherein the handle comprises a fixed part, both the fixed and movable parts configured to be held in the hand of a user via finger holds on each of the handle parts,
  (f) further comprising a rack connected to the fixed handle part and a ratchet connected to the movable handle part and engaging the rack, means for biasing the ratchet into engagement with the rack, and means for disengaging the ratchet from the rack under user control.

10. The electrosurgical handpiece as claimed in claim 9, wherein the means for biasing comprises a roller mounted on the end of the ratchet, a linkage connecting the movable part of the handle to the roller, and a spring incorporated into the linkage.

11. The electrosurgical handpiece as claimed in claim 10, further comprising a finger-operated release lever mounted on the movable part of the handle and connected to the linkage.

12. In combination:
  A. a separable wire-like fibre comprising a long thin flexible electrically-insulated wire or a laser fibre having an active distal end for treating tissue,
  B. a handpiece, comprising:
    (a) an elongated first tubular member having a major longitudinal axis and having a proximal first end and a distal second end and containing an inner channel for receiving the separable wire-like fibre,
    (b) a deflector tip mounted for pivotal movements on the distal second end of the first tubular member, the deflector tip having at least one hole, the separable wire-like fibre being substantially longer than the length of the first tubular member such that the active distal end extends through the hole in the deflector tip and is exposed while the opposite end of the separable wire-like fibre extends out of the proximal end of the first tubular member,
    (c) a handle connected to the first tubular member, the handle having a movable part and a fixed part,
    (d) means connecting the movable part of the handle to the deflector tip such that movements of the movable part of the handle are transmitted to the deflector tip causing the distal exposed end of the separable wire-like fibre to extend in different orientations with respect to the longitudinal axis of the first tubular member,
    (e) a suction port for receiving external suction coupled to the inner channel of the first tubular member, the deflector tip further comprising additional openings such that any suctionable material arising from the treated tissue can be suctioned away via the inner channel and suction port.

13. The combination of claim 12, wherein the separable wire-like fibre is an electrosurgical electrode, further comprising a connector connected to the opposite end of the electrosurgical electrode for connection to electrosurgical apparatus for receiving RF electrosurgical currents.

14. The combination of claim 13, wherein the outside diameter of the separable wire-like fibre is equal to or less than about 1 mm and has an overall length, measured from the connector, of at least about 475 mm.

15. The combination of claim 12, further comprising a removable threaded cap mounted on the proximal end of the first tubular member, the removable cap having an opening through which the separable wire-like fibre passes from the outside into the channel, and means including a resilient sealing member for applying clamping pressure to the separable wire-like fibre when the cap is tightened such that the longitudinal position of the separable wire-like fibre in the channel is maintained.

16. The combination of claim 15, wherein the separable wire-like fibre has a bare end, the first tubular member is straight, further comprising means on the handle under user control for releasably locking any position that the movable and fixed handle parts assume, means for biasing apart the movable and fixed handle parts such that the separable wire-like fibre bare end is aligned with the longitudinal axis of the first tubular member when the means for locking is engaged.

17. The combination of claim 15, wherein the separable wire-like fibre has a bare end, the handle is configured such that, when the movable part is moved away from the fixed part, the deflector tip pivots upward about 45° in discrete steps, and when the movable part is moved toward the fixed part, the deflector tip pivots downward about 15° in discrete steps, the separable wire-like fibre bare end being constrained to follow the movements of the deflector tip and thus pointing upward 45° when the handle parts are apart and pointing downward 15° when the handle parts are separated.

* * * * *